US00PP20396P2

(12) United States Plant Patent
Pieters

(10) Patent No.: US PP20,396 P2
(45) Date of Patent: Oct. 6, 2009

(54) ***CHRYSANTHEMUM* PLANT NAMED 'PPP SON 07'**

(50) Latin Name: *Chrysanthemum morifolium*
Varietal Denomination: PPP SON 07

(75) Inventor: Dirk Pieters, Oostnieuwkerke (BE)

(73) Assignee: Paraty BVBA, Oostnieuwkerke (BE)

( * ) Notice: Subject to any disclaimer, the term of this patent is extended or adjusted under 35 U.S.C. 154(b) by 0 days.

(21) Appl. No.: 12/218,916

(22) Filed: Jul. 18, 2008

(51) Int. Cl.
*A01H 5/00* (2006.01)

(52) U.S. Cl. ..... Plt./287
(58) Field of Classification Search ..... Plt./291, Plt./287
See application file for complete search history.

*Primary Examiner*—June Hwu
(74) *Attorney, Agent, or Firm*—Mark P. Bourgeois

(57) ABSTRACT

A new and distinct *Chrysanthemum* plant cultivar is disclosed, characterized by large decorative type inflorescences, consistent flowering response to short days, blooming consistently after 49 days of short day length, pink inflorescences with a dark red-purple center, free branching habit, and a consistent natural season flowering habit during the second week of September.

1 Drawing Sheet

Latin name of the genus and species: *Chrysanthemum morifolium.*

Variety denomination: 'PPP SON 07'.

BACKGROUND OF THE INVENTION

The new cultivar 'PPP SON 07' is a product of a cross between the male parent 'GEDI TWO CAS' (U.S. Plant Pat. No. 14,428) and the female parent 'GEDI ONE NOV' (U.S. Plant Pat. No. 13,796). The new cultivar was discovered and selected by Dirk Pieters in September of 2002 in Oostnieuwkerke, Belgium.

Asexual reproduction of the new cultivar 'PPP SON 07' by terminal cuttings was performed in Oostnieuwkerke, Belgium and Oxnard, California, and has shown that the unique features of this new cultivar are stable and reproduced true to type on successive generations.

SUMMARY OF THE INVENTION

The cultivar 'PPP SON 07' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'PPP SON 07.' These characteristics in combination distinguish 'PPP SON 07' as a new and distinct *Chrysanthemum* cultivar:

1. Pink, decorative-type inflorescences with dark red-purple center;
2. Free branching habit;
3. Consistent natural season flowering habit during the second week of September; and
4. Consistent flowering response to short days, blooming consistently after 49 days of short day length.

Plants of the new cultivar 'PPP SON 07' are similar to plants of the male parent variety, 'GEDI TWO CAS' in most horticultural characteristics, however plants of the new cultivar 'PPP SON 07' are taller and wider. Also, the female parent 'GEDI TWO CAS' has more inflorescences per lateral branch and a larger inflorescence diameter. Additionally, the ray florets of 'PPP SON 07' are a different color than the male parent. Finally, 'PPP SON 07' has a different inflorescence type than the male parent 'GEDI TWO CAS' and has longer inflorescence longevity.

Plants of the new cultivar 'PPP SON 07' are similar to plants of the female parent variety, 'GEDI ONE NOV' in most horticultural characteristics, however plants of the new cultivar 'PPP SON 07' are smaller in both height and plant spread. Also, the new cultivar 'PPP SON 07' has a smaller inflorescence diameter and longer inflorescence longevity. Finally, 'PPP SON 07' has different color ray florets than the female parent.

In comparison to the commercially available variety 'GEDI TWO KIS' (U.S. Plant Pat. No.14,996), 'PPP SON 07' is smaller in both height and plant spread. Additionally, the comparable variety 'GEDI TWO KIS' has more inflorescences per lateral branch than the new variety 'PPP SON 07' though the new variety 'PPP SON 07' has more ray florets per inflorescence. Further, the inflorescences of the new variety 'PPP SON 07' are a light pink with a darker pink center compared to the single-toned light coral inflorescences of the comparable variety. Finally, the new variety 'PPP SON 07' has longer inflorescence longevity.

BRIEF DESCRIPTION OF THE PHOTOGRAPH

The accompanying photograph illustrates in full color a typical plant of 'PPP SON 07' grown in a 2 gallon container. One cutting was used in the pot, planted mid May and grown under outdoor field conditions. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'PPP SON 07' plants grown in Oxnard, Ventura County, Calif., during the months of May through October 2006. The growing temperature ranged from 12° C. to 15° C. at night to 12° C. to 20° C. during the day. Measurements and numerical values represent averages of typical flowering types.

Botanical classification: *Chrysanthemum morifolium* 'PPP SON 07.'

Commercial classification: Garden-type *Chrysanthemum.*

PROPAGATION

Time to rooting: 7 to 14 days at approximately 21°C.

Root description: Fine, fibrous.

PLANT

Growth habit: Mounding herbaceous perennial.

Height: Approximately 26 cm.

Plant spread: Approximately 42 cm.

Growth rate: Moderate.

Branching characteristics: Free Branching.

Length of lateral branches: Approximately 18 cm.

Number of Leaves per lateral branch: Approximately 28.

Age of plant described: Approximately 141 days.

FOLIAGE

Leaf:

- *Arrangement.*—Alternate single.
- *Average length.*—Approximately 2.5 cm.
- *Average width.*—Approximately 1.7 cm.
- *Shape of blade.*—Ovate.
- *Apex.*—Acuminate.
- *Base.*—Attenuate.
- *Attachment.*—Stalked.
- *Margin.*—Serrate.
- *Texture of top surface.*—Lightly pubescent.
- *Texture of bottom surface.*—Lightly pubescent.
- *Leaf internode length.*—Approximately 1.2 cm.
- *Color.*—Young foliage upper side: Near Green 137A. Young foliage under side: Near Green 137D. Mature foliage upper side: Near Green 137A. Mature foliage under side: Near Green 137D.
- *Venation.*—Type: Palmately net. Venation color upper side: Near Green 138C. Venation color under side: Near Green 138C.

Petiole:

- *Average length.*—Approximately 0.75 cm.
- *Color.*—Near Green 138C.
- *Diameter.*—Approximately 0.3 cm.

BLOOM

Inflorescence:

- *Flowering habit.*—Induced by darkness period greater than 13.5 hours, approximately 49 days of appropriate day length required to induce and develop blooms.
- *Inflorescence form.*—Decorative.
- *Natural flowering season.*—Approximately the second week in September.
- *Number of inflorescences per lateral branch.*—Approximately 9.
- *Inflorescence diameter.*—Approximately 4.2 cm.
- *Inflorescence depth.*—Approximately 1.5 cm.
- *Inflorescence longevity on plant.*—Approximately 28 to 31 days.
- *Persistence.*—Persistent.

Ray florets:

- *Appearance.*—Matte.
- *Texture.*—Smooth.
- *Average number of ray florets per inflorescence.*—241.
- *Shape.*—Oblanceolate.
- *Aspect.*—Flat.
- *Margin.*—Entire.
- *Apex.*—Obtuse.
- *Length.*—Approximately 2.3 cm.
- *Width.*—Approximately 0.6 cm.
- *Color.*—Upper surface at first opening: Near Greyed-Red 182D. Upper surface at maturity: Near Red-Purple 62D. Upper surface at fading: Near Red-Purple 62D. Under surface at first opening: Near Red-Purple 59C. Under surface at maturity: Near Red-Purple 62D with shades of near Red-Purple 59D. Under surface at fading: Near Red-Purple 62D. Center ray florets: Near Red-Purple 64A throughout maturity.

Disc florets:

- *Appearance.*—Shiny.
- *Texture.*—Smooth.
- *Average number of florets per disc.*—Approximately 11.
- *Shape.*—Cylindric.
- *Apex.*—Obtuse.
- *Average length.*—Approximately 0.4 cm.
- *Average width.*—Approximately 0.1 cm.
- Color.—At first opening: Near Yellow 13B. At maturity: Near Yellow 13A. At fading: Near Yellow 13A.

Peduncle:

- *Length.*—At terminal end (shortest): Approximately 4 cm. At lateral end (longest): Approximately 9 cm.
- *Angle to stem.*—Acute.
- *Strength.*—Moderate.
- *Color.*—Near Green 138B.
- *Habit.*—Upright.
- *Diameter.*—Approximately 0.2 cm.
- *Surface texture.*—Lightly pubescent.

Inflorescence bud:

- *Length.*—Approximately 1.2 cm.
- *Diameter.*—Approximately 0.8 cm.
- *Form.*—Globular.
- *Color.*—Near Red-Purple 59C.

Involucral bracts (phyllaries):

- *Appearance.*—Matte.
- *Texture.*—Lightly pubescent.
- *Number.*—Approximately 25.
- *Shape.*—Ovate.
- *Margin.*—Entire.
- *Apex.*—Acute.
- *Length.*—Approximately 0.5 cm.
- *Width.*—Approximately 0.2 cm.
- *Color.*—Upper side: Near Green 137A. Under side: Near Green 137B.

REPRODUCTIVE ORGANS

Ray florets:

- *Number of pistils per floret.*—1.
- *Stigma shape.*—2 branched.
- *Stigma color.*—Near Yellow 5A.
- *Style color.*—Near Green-Yellow 1C.
- *Style length.*—Approximately 0.4 cm.
- *Stamens.*—Absent.

Disc florets:

*Number of pistils per floret.*—1.
*Stigma shape.*—Cylindric.
*Stigma color.*—Near Yellow 13A.
*Style length.*—Approximately 0.2 cm.
*Style color.*—Near Green-Yellow 1D.
*Number of stamens per floret.*—Approximately 5.
*Anther shape.*—Tubular.
*Anther color.*—Near Yellow 13B.
*Pollen color.*—No pollen detected.

OTHER CHARACTERISTICS

Disease resistance: Neither resistance nor susceptibility to diseases or pests has been observed in this variety.

Drought tolerance/cold tolerance: Flowering plants are hardy to low temperatures about −2° C. Non-flowering plants are hardy in the approximate range of 3° C. to −6° C., depending upon duration of cold and amount of moisture in the soil. With adequate water plants are hardy to a high temperature of 45° C.

Fruit/seed production: Commercially, this plant is not used or observed in a stage where seeds would be produced. Therefore, seed production has not been observed.

What is claimed is:

1. A new and distinct cultivar of *Chrysanthemum* plant named 'PPP SON 07 ' as herein illustrated and described.

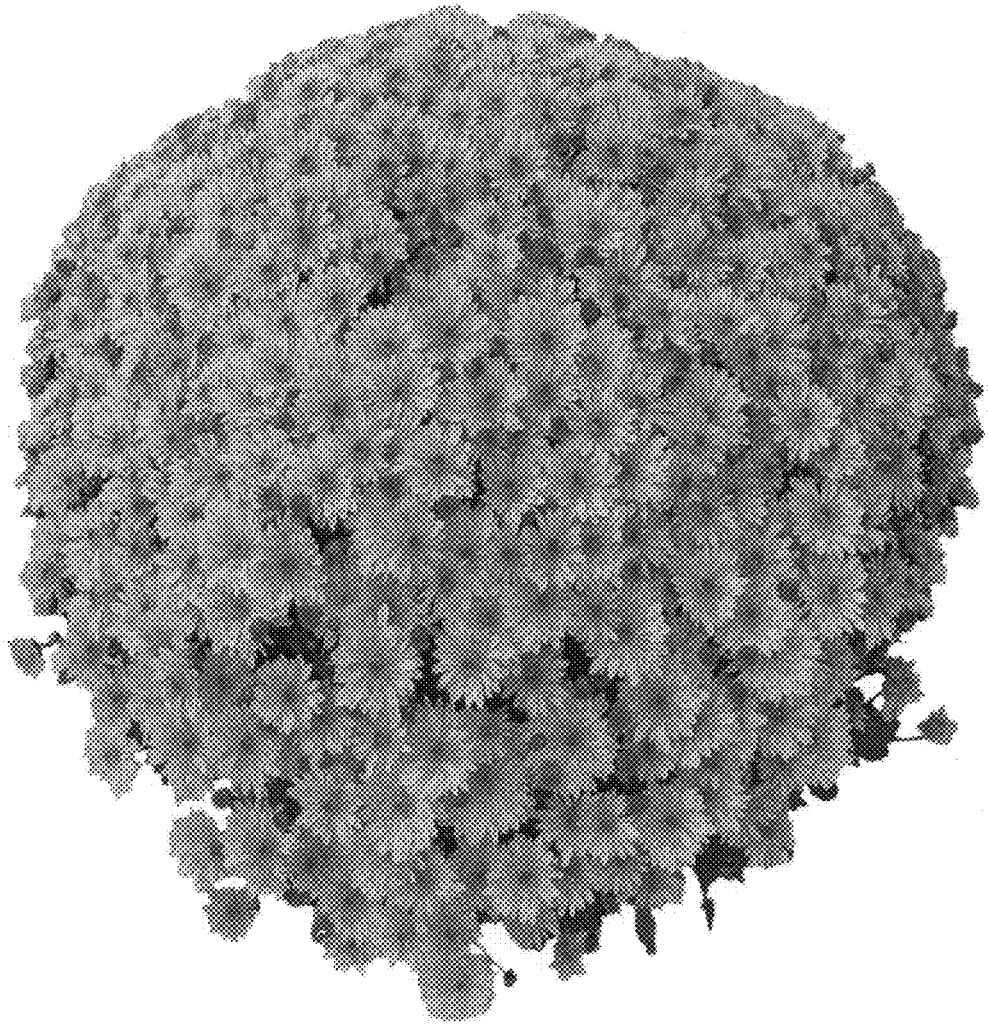

* * * * *